United States Patent [19]

Pieniak et al.

[11] Patent Number: 4,500,315
[45] Date of Patent: Feb. 19, 1985

[54] SUPERTHIN ABSORBENT PRODUCT

[75] Inventors: Heinz A. Pieniak, North Brunswick; Michael J. Iskra, Flemington, both of N.J.

[73] Assignee: Personal Products Company, Milltown, N.J.

[21] Appl. No.: 439,963

[22] Filed: Nov. 8, 1982

[51] Int. Cl.³ .............................................. A61F 13/00
[52] U.S. Cl. ................................................... 604/379
[58] Field of Search ............... 604/378, 379, 380, 381, 604/382, 383; 128/155, 156

[56] References Cited

U.S. PATENT DOCUMENTS

| | | |
|---|---|---|
| Re. 26,151 | 1/1967 | Duncan et al. .................. 604/379 |
| 2,788,003 | 4/1957 | Morin ............................... 604/379 |
| 2,881,769 | 4/1959 | Touey . |
| 2,917,054 | 12/1959 | Touey . |
| 3,008,472 | 11/1961 | Touey . |
| 3,017,304 | 1/1962 | Burgeni ........................... 604/379 |
| 3,612,055 | 10/1971 | Mesek et al. .................... 604/379 |
| 3,670,731 | 6/1972 | Harmon ..................... 128/156 X |
| 3,768,480 | 10/1973 | Mesek et al. .................... 604/379 |
| 3,777,758 | 12/1973 | Mesek et al. .................... 604/379 |
| 3,823,057 | 7/1974 | Roberts et al. . |
| 3,860,003 | 1/1975 | Buell ................................ 604/379 |
| 3,888,256 | 6/1975 | Studinger ........................ 604/379 |
| 3,901,236 | 8/1975 | Assarsson et al. .............. 604/379 |
| 3,903,889 | 9/1975 | Torr . |
| 3,938,522 | 2/1976 | Repke .............................. 604/379 |
| 3,971,373 | 7/1976 | Braun . |
| 3,981,100 | 9/1976 | Weaver et al. . |
| 3,993,553 | 11/1976 | Assarsson . |
| 3,998,988 | 12/1976 | Shimomai et al. . |
| 4,008,353 | 2/1977 | Gross et al. . |
| 4,011,067 | 3/1977 | Carey et al. . |
| 4,044,766 | 8/1977 | Kaczmarzyk et al. ........... 604/379 |
| 4,050,462 | 9/1977 | Woon et al. ..................... 604/379 |
| 4,102,340 | 7/1978 | Mesek et al. .................... 604/379 |
| 4,103,062 | 7/1978 | Aberson et al. ................. 604/379 |
| 4,105,033 | 8/1978 | Chatterjee et al. . |
| 4,118,531 | 10/1978 | Hauser . |
| 4,160,059 | 7/1979 | Samejima . |
| 4,186,165 | 1/1980 | Aberson et al. ................. 604/379 |
| 4,226,237 | 10/1980 | Levesque ........................ 604/379 |
| 4,232,674 | 11/1980 | Melican . |
| 4,235,237 | 11/1980 | Mesek et al. .................... 604/379 |
| 4,259,958 | 4/1981 | Goodbar .......................... 604/379 |
| 4,274,412 | 6/1981 | Austin .............................. 604/379 |
| 4,297,410 | 10/1981 | Tsuchiya et al. . |
| 4,324,245 | 4/1982 | Mesek et al. .................... 604/379 |
| 4,340,057 | 7/1982 | Bloch et al. ..................... 604/379 |
| 4,347,844 | 9/1982 | Ohki et al. . |
| 4,364,992 | 12/1982 | Ito et al. . |
| 4,372,309 | 2/1983 | Fowler . |
| 4,373,519 | 2/1983 | Errede et al. . |
| 4,389,211 | 6/1983 | Lenaghan . |
| 4,401,113 | 8/1983 | Incorvaia . |
| 4,411,660 | 10/1983 | Dawn et al. . |
| 4,414,255 | 11/1983 | Tokuyama et al. . |
| 4,425,130 | 1/1984 | DesMarais . |
| 4,429,001 | 1/1984 | Kolpin et al. . |
| 4,435,178 | 3/1984 | Fitzgerald . |

FOREIGN PATENT DOCUMENTS 1151470 8/1983 Canada .
56-6097 2/1981 Japan .

Primary Examiner—John D. Yasko
Attorney, Agent, or Firm—Martha A. Michaels

[57] ABSTRACT

A superthin absorbent disposable product is provided having an absorbing layer containing superabsorbent and a wicking layer. The product is suitable for use in disposable diapers, sanitary napkins, incontinent pads, wipes and the like.

21 Claims, 11 Drawing Figures

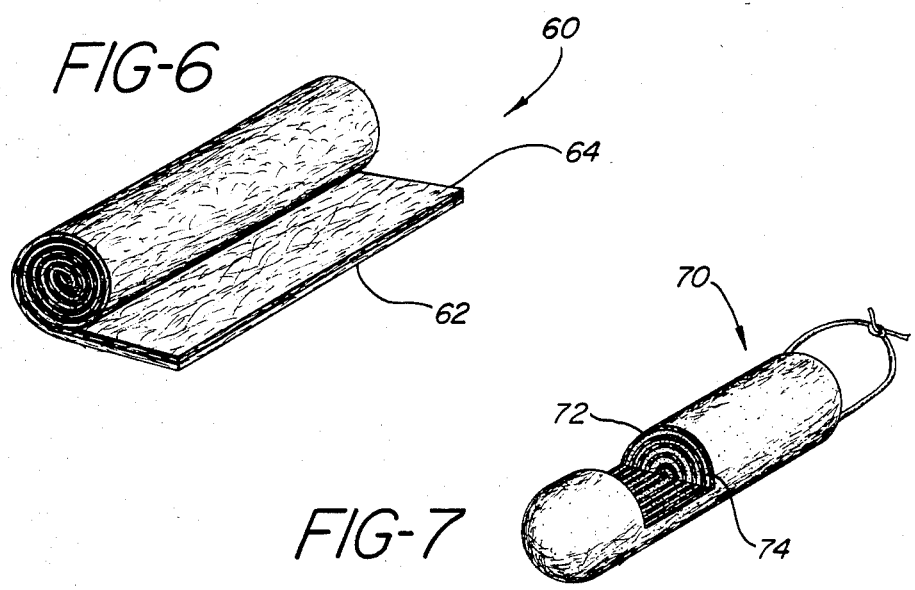
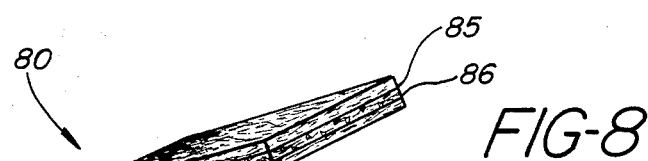

SUPERTHIN ABSORBENT PRODUCT

BACKGROUND OF THE INVENTION

The present invention relates to new and improved absorbent products and, more particularly, to new and improved thin absorbent composites incorporating superabsorbent materials.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between an impermeable backing and a permeable facing and the plies of tissue were used to absorb and, hopefully, contain the liquid within the product. A diaper which utilizes such an absorbent batt is disclosed in U.S. Pat. Re. No. 26,151.

The wadding type of batt was replaced, for the most part, by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the efficiency with which the capacity is used in a diaper or sanitary napkin is poor. The reason for this, is that the fluid to be absorbed is generally deposited in a localized area within the absorbent batt and the ability for the fluid to move along the plane of the batt is poor. The fluid follows the path of least resistance and consequently moves to the closest edge of the batt where it generally is no longer contained and the product leaks.

U.S. Pat. No. 3,017,304 discloses an absorbent product which incorporates in the product a densified, paper-like layer. This paper-like layer acts as a wick, i.e., liquid which is placed on the layer tends to move rapidly along the plane of the layer. When incorporated in combination with fluffed wood pulp fiber, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. This concept of combining a wicking or capillary skin or layer with fluffed wood pulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for absorption. This is especially true if pressure is placed on the batt while wet, for example a baby sitting down on a previously wetted diaper will very often cause the batt to leak.

Recently, elastic leg diapers or stretch diapers have been introduced into the marketplace. Though these diapers provide no better absorbent batt than flat diapers or the prior art diapers, they have indicated improved containment of liquid. Such diapers are disclosed and described in U.S. Pat. Nos. 3,860,003, 4,050,462, and 4,324,245. Though the containment features are better than the prior art products, the elasticized products fit more tightly permitting less air circulation. Frequently, this can become irritating to the skin and the tighter the elastic or the more close fitting the diaper, the greater the irritation. This is especially true adjacent the area where the elastic leg portion of the product contacts the wearer.

A number of years ago "superabsorbent materials", i.e., materials which will absorb many times their weight of liquid, were developed. Since the development of such materials, people have been trying to incorporate them in absorbent products such as diapers and sanitary napkins to enhance the absorptive performance of these products. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water insoluble cross-linked hydrocolloid polymer as the superabsorbent material.

Even though superabsorbent materials have been available for some time, they have not gained wide acceptance in absorbent products such as disposable diapers and sanitary napkins. A primary reason for this lack of acceptance of the superabsorbents is failure to develop a product capable of economically utilizing the highly increased absorptive capacity of the superabsorbent material. In order to economically utilize a superabsorbent, the liquid being absorbed must be transported to the superabsorbent material. In other words, the superabsorbent material must be placed in contact with the liquid. Furthermore, as the superabsorbent material absorbs the liquid, it must be allowed to swell. If the superabsorbent is prevented from swelling, it will cease absorbing liquid. Hence if the superabsorbent material is to function in diapers and sanitary napkins wherein the liquid to be absorbed is placed in a small void area, the structure of the absorbent layer containing superabsorbent materials appears to be critical. Over the years a number of techniques have been disclosed in an attempt to provide structures which make efficient use of the superabsorbent material. Such products are disclosed in U.S. Pat. Nos. 4,103,062, 4,102,340, and 4,235,237. In addition, methods for incorporating superabsorbents into suitable layers or suitable configurations which can be placed in an absorbent product, are disclosed in U.S. Pat. Nos. 4,186,165 and 4,340,057. To date, none of these products has met with any substantial commercial success.

The present invention provides a new and improved absorbent composite which utilizes a substantial portion of the absorptive capacity of superabsorbent materials. This new composite makes use of this capacity even though the liquid being absorbed is placed on the composite in a localized area. Furthermore and unexpectedly, the new absorbent composite maintains a desired softness, flexibility, and conformability while efficiently using the superabsorbent material thereby making it especially suitable for use in disposable diapers. In addition and unexpectedly, the new composite contains the liquid absorbed in the composite even without the use of elastic leg members in the product. Surprisingly, the new composite will contain absorbed liquid even when pressure is placed upon the product during use.

SUMMARY OF THE INVENTION

The present invention provides a disposable absorbent, compressed composite comprising an absorbing layer, a transition area, and a wicking layer. The absorbing layer is comprised of a fibrous web having a dry bulk recovery of at least about 60 percent, an initial dry bulk of at least about 20 cc/gm and a weight of less than about 2 oz/yd$^2$ (68 gm/m$^2$). The absorbing layer has superabsorbent material in the form of a plurality of particles or globules of superabsorbent material disposed in a random and intermittent arrangement throughout the absorbing layer. The particles or globules are of a size and spacing so that they do not interfere with the absorption of liquid by adjacent particles. The wicking layer is comprised of particles which are cellulosic fibers, peat moss, or mixtures thereof. These particles are randomly disposed, frictionally entangled and sufficiently closely spaced to adjacent particles to assist in promoting rapid movement of liquid along the plane of the layer. The transition area is comprised of portions of the entangled particles of the wicking layer extending into and becoming integral with the absorbing layer. Some portions of the wicking layer particles are in intimate contact with some of the superabsorbent material. The compressed composite, in its compressed form, is less than one-half its thickness in an uncompressed form and upon contact with liquid regains at least 75 percent of its thickness in uncompressed form.

The absorbent system of the present invention is comprised of at least two layers to form a thin, absorbent structure. One layer functions primarily as a liquid transport media, i.e., a wicking layer. The other layer functions as an absorbent reservoir to retain volumes of body fluids. This layer is referred to as the absorbing layer. The absorbing layer is a low density, resilient, fibrous web consisting of randomly disposed, frictionally entangled fibers which result in a web having a dry bulk recovery of at least 60 percent, an initial dry bulk of at least 20 cc/gm and a weight less than about 2 oz/yd$^2$. The fibrous web making up the absorbing layer is used to spacially distribute superabsorbent material so that upon exposure to an aqueous fluid, swelling occurs with minimal interference from adjacent superabsorbent material. The transporting or wicking layer is a high density structure made of particles selected from the group consisting of cellulosic fibers, peak moss, or mixtures thereof. One layer is superimposed upon the other by air laying with or without vacuum, water casting or the like. The two layers are compressed at a pressure adequate to collapse the total structure to promote intimate contact between the wicking layer and the absorbing layer. In fact, at least portions of some of the particles of the wicking layer extend into and become integral with the absorbing layer providing a transition area wherein some of the particles come in contact with some of the superabsorbent material interspersed in the absorbing layer. Generally, the compression is carried out in the presence of a moisture content of at least about 10 percent so that some of the superabsorbent is soft and tacky and upon compression holds the absorbing layer in a compressed state. When being used, the compressed composite product is exposed to a fluid including body fluids such as urine, menstrual fluid, or other fluids. Generally, the fluids are deposited in a localized area on one surface of the compressed composite product. The wicking layer immediately transports any excess fluid in any given area to other areas in the x,y plane of the layered structure. As fluid contacts the unwetted areas of the structure, the superabsorbent in intimate contact with the wicking layer begins to form a gel and soften. As softening occurs, the absorbing layer is gradually released from its compressed state and recovers substantially its original low density nature due to the fibrous web resilience. This low density provides storage areas for the liquid and the superabsorbent continues to swell with minimal interference from adjacent superabsorbent material. As the liquid front moves along the x, y plane, it triggers sequential release of the resilient structure to allow fluid migration in the z direction as well, i.e., in the direction of the thickness of the product.

BRIEF DESCRIPTION OF THE DRAWINGS

FIG. 6 is a perspective view of a blank for a tampon embodying the present invention;

FIG. 7 is a perspective view of a tampon made from the blank shown is FIG. 6;

FIG. 8 is a perspective view of another blank for a tampon embodying the present invention;

FIG. 9 is a cross-sectional view of a tampon made from the blank of FIG. 8; and

DETAILED DESCRIPTION OF THE INVENTION

Figure 1:
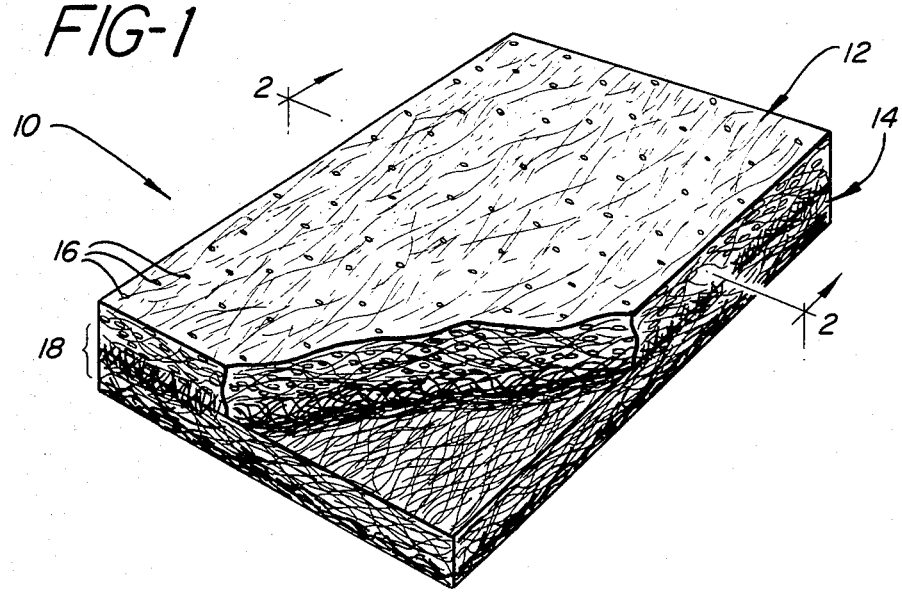
FIG. 1 is a perspective view illustrating one embodiment of the present invention.

Referring now to the drawings, FIG. 1 represents a perspective view of an absorbent product of the present invention. The absorbent product 10 has a fibrous web as an absorbing layer 12. Interspersed and fixed in the absorbing layer are superabsorbent particles 16. Immediately associated with the absorbing layer is the wicking layer 14. Some of the particles of the wicking layer 14 extend into and become integral with the absorbing layer 12 thus forming the transition area 18. The structure depicted in FIG. 1 is in an uncompressed state for ease of illustration. Upon compression some of the particles in the wicking layer 14 will extend into and become integral with the fibers of the absorbing layer. These wicking layer particles consequently will also be in contact with the superabsorbent particles. Generally at least 10 percent moisture is present when the structure is compressed under a pressure sufficient to compact the structure and cause the softened surface of the superabsorbent material to provide the necessary adhesion to the fibers with absorbing layer so that they remain in a compacted state.

Figure 2:
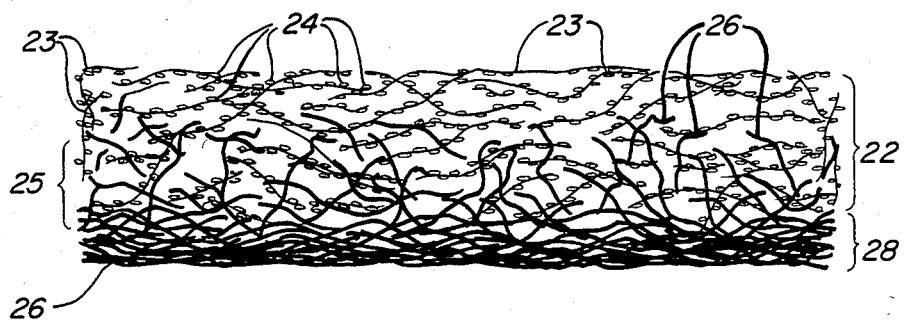
FIG. 2 is an enlarged cross-sectional view through lines 2—2 of FIG. 1.
Figure 2A:
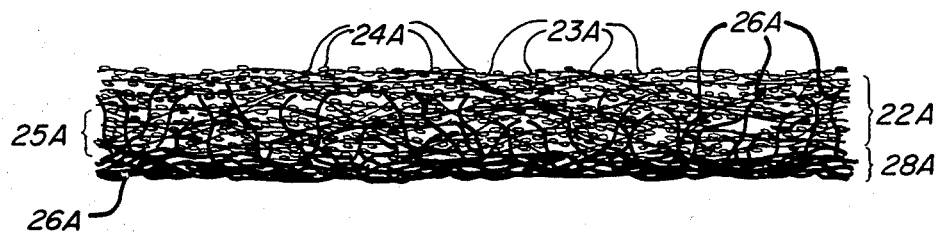
FIG. 2A is an enlarged cross-sectional view through lines 2—2 of FIG. 1 but after compression.

FIG. 2 provides a cross-sectional view along line 2—2 of FIG. 1 showing in detail the relationship of the layers of the absorbent product. The absorbing layer 22 is made from resilient fibers. The superabsorbent particles 24 are interspersed and fixed among the resilient fibers 23. The wicking layer 28 is comprised of particles 26 some of which extend into and become integral with the absorbing layer. The transition area 25 contains the wicking layer particles 26 in contact with a portion of the wicking layer 28 so as to be in intimate contact with some of the superabsorbent particles 24. FIG. 2A depicts the structure of FIG. 2 in a compressed state showing that the absorbing layer 23A has been substantially reduced in thickness and the wicking layer 28A has also been reduced in thickness but extends considerably into and becomes integral with the absorbing layer to form the transition area 25A. Although the superabsorbent particles 24A are closer to each other, there is still sufficient opportunity for liquid to pass between the particles and upon their softening, the resilient fibers of the absorbing layer are released to return the layer to its original low density form.

Figure 3:
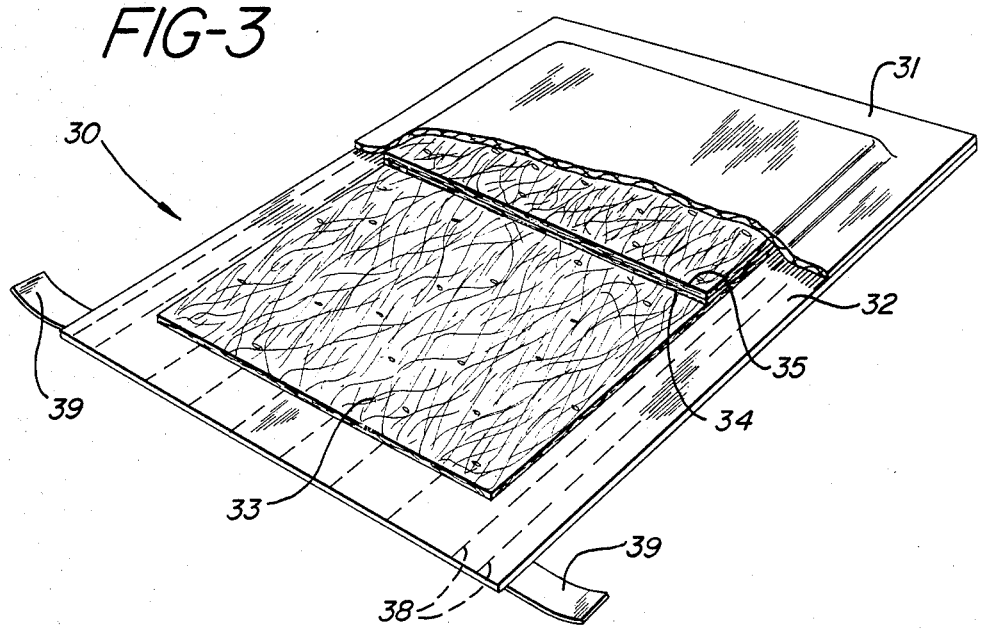
FIG. 3 is a perspective view illustrating another embodiment of the present invention.

Referring now to FIG. 3, a diaper 30 is depicted. A moisture-pervious facing such as a nonwoven fabric 31 provides the diaper surface. A moisture-impervious substance, such as polyethylene, forms the moisture-proof backing 32 of the diaper. This particular diaper structure 30 contains one complete compressed composite layer, 33, and two layers, 34 and 35, which are placed only in the front portion of the diaper, each layer being the absorbent structure shown in FIG. 1, but in a compressed state. In order to seal the diaper in the margins, glue lines 38 are provided. To secure the diaper about the waist of the wearer, tape tabs 39 are provided. The diaper product 30 provides an exceptionally thin diaper which accepts liquid and rapidly transports it to all areas of the absorbent structures 33, 34, and 35. In producing a diaper in accordance with FIG. 3, one or more layers of the absorbent structure may be used. Generally, the wicking layer is placed closest to the facing. However, when multiple composites are being used, the remaining composites may be placed with the wicking layer either toward the facing or the backing. Even using three layers of the absorbent structure of the present invention a diaper is provided having less thickness than a commercial fluff pulp diaper presently available.

Figure 4:
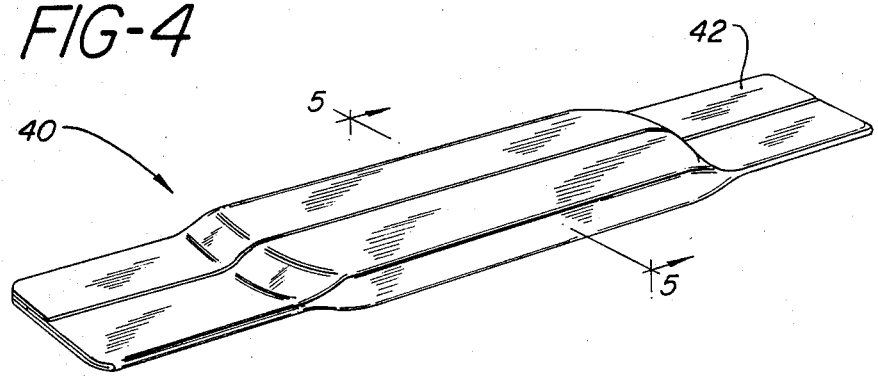
FIG. 4 is a perspective view illustrating still another embodiment of the present invention.
Figure 5:
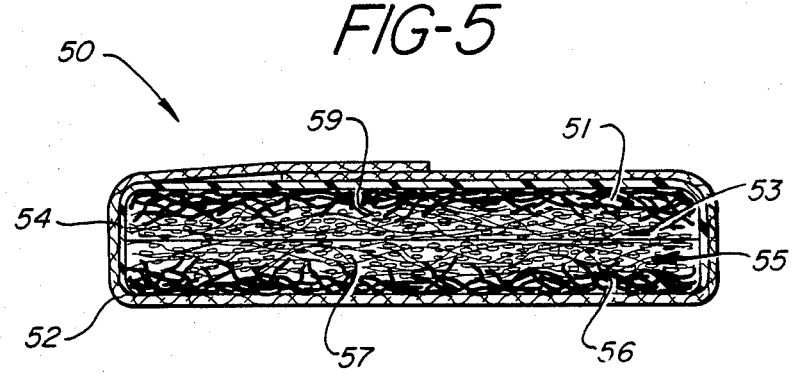
FIG. 5 is an enlarged cross-sectional view through lines 5—5 of FIG. 4.

Referring now to FIG. 4, a sanitary napkin 40 is provided having a fabric overlay 42. FIG. 5 is a cross sectional view along line 5—5 of FIG. 4 showing the layer construction in the napkin depicted in FIG. 4. The structure 50 has a moisture-permeable nonwoven fabric 52. Surrounding the sides and bottom area of the structure is a moisture-impermeable wrap 54. Immediately associated with the exterior wrap 52 in the fluid receiving area is an absorbent structure 55 with a wicking layer 56 in immediate contact with the exterior wrap. Thus, as the liquid enters the absorbent structure 55 through the exterior wrap 52 it is immediately transported in the wicking layer 56. The liquid then migrates through the absorbing layer 57 and into the adjacent absorbing layer 59 of absorbent structure 53. As the liquid continues its progression throughout the entire structure 50, it proceeds to wicking layer 51 of absorbent structure 53 and is transported in the x,y plane along the moisture-impermeable wrap 54. The two compressed composite structures 53 and 55 provide a sanitary napkin of less than half the thickness of the conventional fibrous batt napkin.

FIG. 6 depicts a blank 60 for manufacturing a tampon consisting of a single absorbent structure depicted in FIG. 1 but in a compressed state. The surface 64 is the surface of the absorbing layer and is a nonwoven fabric of wet-resilient fibers having interspersed therein superabsorbent. The surface 62 is a layer of wood pulp fibers closely associated with the absorbing layer. The two layers are in a compressed state resulting in a transition area 63. The blank 60 is rolled and shaped so as to form the tampon 70 depicted in FIG. 7. The broken away portion of the drawing shows the absorbing layer 74 and the wicking layer 72 and the transition area 73.

In still another tampon structure depicted in FIG. 8, a blank 80 is provided with a wicking layer 81, an absorbing layer 83, and another wicking layer 82 on the opposite surface of the absorbing layer. This structure provides to transition areas 85 and 86 upon compression. Superabsorbent particles 84 are interspersed and fixed in the absorbing layer 83. The tampon blank 80 is folded over and shaped to provide the tampon 90 in FIG. 9. In FIG. 9 the tampon is cut away to provide a cross-sectional view showing the two wicking layers 91 and 92 with the absorbing layer 93 sandwiched in between. The absorbing layer contains the superabsorbent particles 94. Transition areas 95 and 96 provide the necessary contact of the wicking layer particles with the absorbing layer superabsorbent material.

Figure 10:
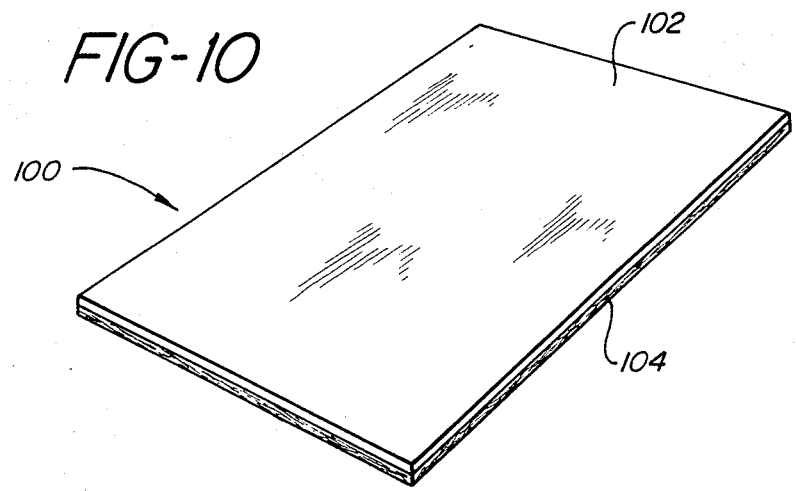
FIG. 10 is a perspective view of a wipe illustrating another embodiment of the present invention.

FIG. 10 depicts a wipe 100 wherein a polypropylene nonwoven fabric 102 forms a substrate. Affixed to the substrate 102 is a compressed composite 104 with its absorbing layer superimposed on the substrate 102 and the wicking layer forming the opposing surface.

These and other products such as incontinent pads, wound dressings, and the like may be made from the absorbent structure depicted in FIG. 1 but in a compressed state.

The absorbing layer is a fibrous web generally formed from synthetic staple fibers such as polyethylene, polypropylene, polyester, nylon, and the like. However, cellulosic fibers such as rayon may be used. The fibrous web has a dry bulk recovery of at least about 60 percent, an initial dry bulk of at least about 20 cc/gm and a weight of less than about 2 oz/yd$^2$. The resulting resiliency of the fibrous web permits the absorbing layer to regain at least 75 percent of its original thickness when it is released from its compressed state as liquid penetrates the absorbent product. The fibrous web may be formed by dry laying or wet laying fibers but in such a manner as to provide the necessary low density structure. In one embodiment, staple polyester fibers are air-laid to form a web which web is subsequently lightly bonded by passing hot air through the fibers in order to provide some degree of integrity to the web structure.

The superabsorbent material present in an intermittently dispersed form in the absorbing layer is generally a water-insoluble but water-swellable polymeric substance capable of absorbing water in an amount which is at least 10 times the weight of the substance in its dry form. The superabsorbent material is in the form of particles which may be in the shape of fibers, spheres, bits of film, or the like, or may be applied in the form of a liquid monomer which is subsequently polymerized. Generally, the polymerized liquid monomer provides globules and bits of film-like particles in the structure.

The particles or fibers may be described chemically as having a backbone of natural or synthetic polymers with hydrophyllic groups or polymers containing hydrophyllic groups being chemically bonded to the backbone or an intimate admixture therewith. Included in this case of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophyllic. Such modified polymers may also be cross-linked to enhance their hydrophyllicity and render them water-insoluble.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophyllic chain of the general formula

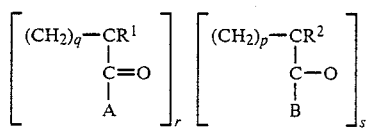

wherein A and B are selected from the group consisting of —$OR^3$, —O (alkali metal), —$OHNH_3$, —$NH_2$, wherein $R^1$, $R^2$ and $R^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1 and q is an integer having a value of 1 to 4. The preferred hydrophyllic chains are hydrolyzed polyacrylonitrile chains and copolymers of polyacrylamide and sodium polyacrylate.

In addition to modified natural and regenerated polymers, the hydrocolloid particle component may comprise wholly synthetic hydrophyllic particles. Examples of those now known in the art are polyacrylonitrile fibers which may be modified by grafting moieties thereon such as polyvinyl alcohol chains, polyvinyl alcohol itself, hydrophyllic polyurethane, poly(alkyl phosphonates), partially hydrolyzed polyacrylamides (e.g., poly(n-N-Dimethyl acrylamide), sulfonated polystyrene, or poly(alkylene oxide). These highly hydrophyllic synthetic polymers may be modified by other chemical treatments such as cross-linking or hydrolysis. Further examples known in the art are the non-ionic hydrophyllic polymers such as polyoxyethylene, polyoxypropylene and mixtures thereof which have been suitably cross-linked, either chemically or with radiation. Still another more recent type is a derivative of isobutylene-maleic anhydride copolymer.

Hydrophyllic polymers formed from water-soluble acrylate monomers, such as sodium, potassium, ammonium (or combination of cations), acrylate, may be placed on the absorbing layer by spraying or otherwise placing a solution thereon followed by polymerization and cross-linking, for example, by irradiation.

Any superabsorbent which absorbs large amounts of liquids is suitable for use in the absorbing layer of the present invention.

The wicking layer is comprised of cellulosic fibers, peat moss, or mixtures thereof. These cellulosic fibers include wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers or peat moss or mixtures thereof are placed in such a way as to form a layer in which the particles are immediately adjacent one another so as to promote wicking of liquid in the plane of the layer.

The wicking layer can be preformed and placed next to the absorbing layer before compression or the wicking layer particles can be air-laid or wet-laid on to the absorbing layer before compression.

The transition area is a region formed at the junction of the absorbing layer and the wicking layer. Some of the particles of the wicking layer extend into and become integral with the absorbing layer. The region in which the majority of the extending particles lie is identified as the transition area. In the transition area, there is a composite of absorbing layer fibers, superabsorbent material, and wicking layer particles. The wicking layer particles which have extended into the absorbing layer are in intimate contact with some of the superabsorbent material of the absorbing layer. This permits the liquid to commence its migration in the z direction to reach the superabsorbent material. As the liquid progresses in the z direction, the superabsorbent material becomes soft and releases the absorbing layer fibers which permit the absorbing layer to return to at least 75 percent of its uncompressed thickness. As the absorbing layer returns to its uncompressed thickness, larger void areas are provided for storage of the liquid and for increased swelling of the superabsorbent material as it absorbs the liquid residing in the void areas.

In order for the absorbing layer fibrous web to provide the necessary medium for absorbing liquid, the fibrous web has a dry bulk recovery of at least 60 percent, an initial dry bulk of at least about 20 cc/gm, and a weight of less than about 2 oz/yd². The initial dry bulk is the area times thickness of the layer under a load of 0.01 pounds per square inch calculated in cubic centimeters. This value is divided by the weight in grams in order to provide the measurement in cubic centimeters per gram. The dry bulk recovery is obtained by subjecting the web to a load of 1.75 psi for five minutes, removing the load and allowing the web to rest for one minute, subjecting the web to a load of 0.01 psi for one minute and then measure the final dry bulk. The dry bulk recovery is the final bulk divided by the initial bulk expressed in percent. If the fibrous web can provide this dry bulk recovery and has an initial dry bulk of at least 20 cc/gm with a web weight of less than 2 oz/yd², the fibrous web will meet the requirements of the absorbing layer. When the fibrous web has these requirements, it can retain superabsorbent material up to at least 1,500 percent of the dry basis weight of the web. It is preferable that the web contain 200 percent to 1,500 percent by weight dry basis superabsorbent to the dry basis weight of the web. Most preferred is a range from about 400 percent to about 1,200 percent.

Examples of methods of preparing the absorbent product of the present invention are as follows. These examples are not intended to be limiting in any way and extensions and modifications thereof without departure from the spirit and scope of the invention will become apparent from these examples.

EXAMPLE 1

An absorbing layer is formed by polyester fibers by dry laying the fibers, i.e., by air laying or carding to form a web. The web is then subjected to heat bonding to provide integrity to the web. The resulting web is 25 grams per square meter, basis weight. The specific polyester fibers used are identified as Type 99 Hollofil fibers manufactured and sold by E. I. Dupont Company. The fibrous web is placed on top of a sheet of wet-formed chemically delignified wood pulp fibers, the fibers being identified as RayFloc JLD manufactured by ITT Rayonair having a basis weight of 50 grams per square meter. A powder superabsorbent polymer is uniformly sprinkled onto and into the nonwoven fiber polyester structure at a concentration of 200 grams per square meter. The particular superabsorbent used is identified as Permasorb 10 manufactured by National Starch and Chemical Corporation. The structure is sprayed with a mist of water on the polyester side and then subjected to a compression force of 640 psi for 30 seconds. On release of the pressure the structure remains compressed and is available to function as an absorbent product described in this invention.

EXAMPLE 2

Using the same polyester fibrous web formed in Example 1, the web is coated by flooding it with an aqueous solution of 38% solids, the solution solids being 90% sodium acrylate and 10% acrylic acid. Vacuum in the amount of one inch of mercury is used to withdraw the excess solution from the web. The web is then subjected to 6 megarads of electron beam radiation. The web is again flooded subjected to vacuum and irradiated. A third time after flooding and the vacuum treatment, the web is subjected to 12 megarads of electron beam radiation to polymerize and crosslink the monomer and form polysodium acrylate (PSA) affixed to the polyester fiber. Two hundred grams/m$^2$ of PSA is present in the substrate. This is equivalent to 800% dry-add-on. This coated substrate is passed beneath a hammer mill that deposits chemically treated wood pulp fibers onto the polyester web. Vacuum is applied under the polyester web so as to cause some of the pulp fibers to at least partially migrate into the polyester web and become integral therewith. The major portion of the wood pulp fibers will reside on the surface providing a layer containing wood pulp fibers of 50 gms/m$^2$. The surface of the pulp layer is sprayed with water so that the total moisture content of the pulp is 10 percent by weight. This structure is compressed at a level of 640 psi for 30 seconds. Upon release of pressure the pulp has formed into a high density layer with a capillary size suitable for liquid wicking and the resilient fiber layer remains compressed. Upon use of this structure when liquid contacts the surface and migration of the liquid into the product takes place, the superabsorbent become soft and releases the resilient fibers so that the thickness of the absorbent structure increases markedly. This provides an area for storage of liquid wherein the capillary size is large.

EXAMPLE 3

The same polyester web is treated with a wood pulp fiber-water slurry which is drained through the polyester fiber web so that a pulp deposit of 50 grams per square meter is formed on one side of the polyester web. The two layered sheet is dried. Onto the polyester web side of the sheet is sprayed the same monomer solution as in Example 1, so that practically no monomer solution contacts the wood pulp fiber layer. As before, the sample is coated and treated three times providing 800% dry-add-on of PSA. The resulting structure at a moisture content of approximately 50 percent by weight is compressed at a level of 640 psi for 30 seconds. Upon release of the pressure the structure remains compressed and is ready for use as taught hereinbefore.

When placing the superabsorbent into the absorbing layer, it is important that the superabsorbent be in the proper quantity and adequately spaced so that gel blocking does not take place. Gel blocking occurs when superabsorbent is in sufficient quantity or the particles are sufficiently close together that as they swell a layer of gel is formed and additional liquid cannot penetrate that layer.

The moisture layer of the two layers prior to compression preferably is sufficient to make the exterior surface of the superabsorbent tacky so as to provide a temporary bonding of the wet resilient fibers under compression. Thus, the compressed composite structure remains compressed until it is in contact with sufficient liquid for the superabsorbent to begin swelling and to thereby release the bonds formed with the resilient fibers.

The structure is compressed sufficiently to reduce the thickness of the structure by at least 50 percent and the pressure must be sufficient to cause the composite to remain compact after the pressure is released.

Other methods for preparing the absorbent product of the present invention may be used.

From the foregoing it will be observed that numerous variations and modifications may be effected without departing from the true spirit and scope of the novel concept of this invention.

We claim:

1. A disposable absorbent compressed composite laminate comprising a first layer, a second layer, and a transition area integrally and intimately connecting said first and second layers and being substantially coextensive therewith, said first layer comprising a fibrous web having a dry bulk recovery of at least about 60 percent, an initial dry bulk of at least about 20 cc/gm, and a weight less than about 2 oz/yd$^2$, and a plurality of particles or globules of superabsorbent material disposed randomly and intermittently throughout said first layer, said particles or globules being of a size and spacing whereby said particles do not interfere with the absorption of liquid by adjacent particles, said second layer comprising randomly disposed, frictionally entangled particles selected from the group consisting of cellulosic fibers, peat moss, and mixtures thereof, said particles being sufficiently closely spaced to adjacent particles to promote rapid movement of liquid along the plane of said layer, and said transition area comprising portions of said entangled particles extending into and becoming integral with said first layer with portions of said entangled particles in intimate contact with said superabsorbent material, said composite laminate in its compressed form being less than one-half its thickness in an uncompressed form and upon contact with liquid, regains at least 75 percent of its thickness in uncompressed form.

2. The compressed composite laminate of claim 1 wherein said first layer is a nonwoven fabric of synthetic staple fibers.

3. The compressed composite of claim 2 wherein the nonwoven fabric is polyester.

4. The compressed composite laminate of claim 1 wherein said second layer is chemically delignified wood pulp fibers.

5. The compressed composite laminate of claim 1 wherein said second layer is peat moss.

6. The compressed composite laminate of claim 1 wherein the superabsorbent material is present in an amount from about 200 percent to about 1,500 percent by dry weight based on the dry weight of said fibrous web.

7. A disposable absorbent compressed composite comprising an absorbing layer, a transition area, and a wicking layer, said absorbing layer comprising a fibrous web having a dry bulk recovery of at least about 60 percent, an initial dry bulk of at least about 20 cc/gm, and a weight of less than about 2 oz/yd$^2$, said wicking layer comprising particles selected from the group consisting of cellulosic fibers, peat moss, and mixtures thereof, some of said particles extending into and becoming integral with said absorbing layer to provide said transition area, said absorbing layer having interspersed therein superabsorbent material arranged so as not to gel block and present in an amount between about 200 percent and 1,500 percent dry weight basis based on said fibrous web dry weight basis, said composite in its compressed form being less than one-half its thickness in an uncompressed form and upon contact with liquid regains at least 75 percent of its thickness in uncompressed form.

8. The compressed composite of claim 7 wherein said absorbing layer is a nonwoven fabric of synthetic staple fibers.

9. The compressed composite of claim 8 wherein the nonwoven fabric is polyester.

10. The compressed composite of claim 7 wherein said wicking layer is chemically delignified wood pulp fibers.

11. The compressed composite of claim 7 wherein said wicking layer is peat moss.

12. The compressed composite of claim 7 wherein said superabsorbent is present in an amount from about 400 percent to about 1,200 percent dry weight basis based on said fibrous web dry weight basis.

13. A disposable diaper containing an absorbent pad wherein said absorbent pad is an absorbent compressed composite comprising an absorbing layer, a transition area, and a wicking layer, said absorbing layer comprising a fibrous web having a dry bulk recovery of at least about 60 percent, an initial dry bulk of at least about 20 cc/gm, and a weight of less than about 2 oz/yd$^2$, said wicking layer comprising particles selected from the group consisting of cellulosic fibers, peat moss, and mixtures thereof, some of said particles extending into and becoming integral with said absorbing layer to provide said transition area, said absorbing layer having interspersed therein superabsorbent material arranged so as not to gel block and present in an amount between about 200 percent and 1,500 percent dry weight basis based on said fibrous web dry weight basis, said composite in its compressed form being less than one-half its thickness in an uncompressed form and upon contact with liquid regains at least 75 percent of its thickness in uncompressed form.

14. The disposable diaper of claim 13 wherein said absorbent pad is comprised of two or more absorbent compressed composites.

15. The disposable diaper of claim 13 wherein the absorbing layer of said compressed composite is comprised of a polyester nonwoven web and the wicking layer of said compressed composite is comprised of chemically delignified wood pulp fibers.

16. The disposable diaper of claim 13 wherein said compressed composite is comprised of an absorbing layer sandwiched between two wicking layers.

17. A sanitary napkin comprising an absorbent structure partially encompassed by a liquid barrier with a moisture-permeable overwrap, said absorbent structure being a disposable absorbent compressed composite laminate comprising a first layer, a second layer, and a transition area integrally and intimately connecting said first and second layers and being substantially coextensive therewith, said first layer comprising a fibrous web having a dry bulk recovery of at least about 60 percent, an initial dry bulk of at least about 20 cc/gm, and a weight less than about 2 oz/yd$^2$, and a plurality of particles or globules of superabsorbent material disposed randomly and intermittently throughout said first layer, said particles or globules being of a size and spacing whereby said particles do not interfere with the absorption of liquid by adjacent particles, said second layer comprising randomly disposed frictionally entangled particles selected from the group consisting of cellulosic fibers, peat moss, and mixtures thereof, said particles being sufficiently closely spaced to adjacent particles to promote rapid movement of liquid along the plane of said layer, and said transition area comprising portions of said entangled particles extending into and becoming integral with said first layer with portions of said entangled particles in intimate contact with said superabsorbent material, said composite laminate in its compressed form being less than one-half its thickness in an uncompressed form and upon contact with liquid, regains at least 75 percent of its thickness in uncompressed form.

18. The sanitary napkin of claim 17 wherein said absorbent structure comprises two compressed composite laminates superimposed one upon the other with the absorbing layers immediately adjacent one another.

19. A tampon having as its absorbent portion a disposable absorbent compressed composite laminate comprising a disposable absorbent compressed composite laminate comprising a first layer, a second layer, and a transition area integrally and intimately connecting said first and second layers and being substantially coextensive therewith, said first layer comprising a fibrous web having a dry bulk recovery of at least about 60 percent, an initial dry bulk of at least about 20 cc/gm, and a weight less than about 2 oz/yd$^2$, and a plurality of particles or globules of superabsorbent material disposed randomly and intermittently throughout said first layer, said particles or globules being of a size and spacing whereby said particles do not interfere with the absorption of liquid by adjacent particles, said second layer comprising randomly disposed frictionally entangled particles selected from the group consisting of cellulosic fibers, peat moss, and mixtures thereof, said particles being sufficiently closely spaced to adjacent particles to promote rapid movement of liquid along the plane of said layer, and said transition area comprising portions of said entangled particles extending into and becoming integral with said first layer with portions of said entangled particles in intimate contact with said superabsorbent material, said composite laminate in its compressed form being less than one-half its thickness in an uncompressed form and upon contact with liquid, regains at least 75 percent of its thickness in uncompressed form.

20. The tampon of claim 19 wherein said compressed composite laminate is comprised of two wicking layers one on each side of an absorbing layer.

21. A wipe comprising a nonwoven fabric as a substrate having affixed thereto a disposable absorbent compressed composite laminate comprising a first layer, a second layer, and a transition area integrally and intimately connecting said first and second layers and being substantially coextensive therewith, said first layer comprising a fibrous web having a dry bulk recovery of at least about 60 percent, an initial dry bulk of at least about 20 cc/gm, and a weight less than about 2 oz/yd$^2$, and a plurality of particles or globules of superabsorbent material disposed randomly and intermittently throughout said first layer, said particles or globules being of a size and spacing whereby said particles do not interfere with the absorption of liquid by adjacent particles, said second layer comprising randomly disposed frictionally entangled particles selected from the group consisting of cellulosic fibers, peat moss, and mixtures thereof, said particles being sufficiently closely spaced to adjacent particles to promote rapid movement of liquid along the plane of said layer, and said transition area comprising portions of said entangled particles extending into and becoming integral with said first layer with portions of said entangled particles in intimate contact with said superabsorbent material, said composite laminate in its compressed form being less than one-half its thickness in an uncompressed form and upon contact with liquid, regains at least 75 percent of its thickness in uncompressed form.

\* \* \* \* \*